(12) United States Patent
Yamazaki et al.

(10) Patent No.: US 6,860,835 B2
(45) Date of Patent: Mar. 1, 2005

(54) EXERCISE SIGNAL GENERATOR OF EXERCISE LOAD METER

(75) Inventors: Iwao Yamazaki, Tokyo (JP); Yoshihiro Izawa, Tokyo (JP); Kimiyo Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/275,967

(22) PCT Filed: May 14, 2001

(86) PCT No.: PCT/JP01/03991
§ 371 (c)(1),
(2), (4) Date: Nov. 18, 2002

(87) PCT Pub. No.: WO01/87160
PCT Pub. Date: Nov. 22, 2001

(65) Prior Publication Data
US 2003/0114272 A1  Jun. 19, 2003

(30) Foreign Application Priority Data
May 18, 2000  (JP) ........................................ 2000-146139
Jun. 6, 2000  (JP) ........................................ 2000-169429

(51) Int. Cl.[7] ............................................ A63B 21/00
(52) U.S. Cl. ................................ 482/8; 482/3; 235/105
(58) Field of Search ............................. 482/1–9, 51, 74, 482/900–902; 73/488–490, 379.01; 235/105

(56) References Cited

U.S. PATENT DOCUMENTS 4,489,934 A * 12/1984 Miller ......................... 482/82
5,800,311 A *  9/1998 Chuang ....................... 482/44
6,254,513 B1 *  7/2001 Takenaka et al. .............. 482/3

* cited by examiner

*Primary Examiner*—Glenn E. Richman
(74) *Attorney, Agent, or Firm*—Bacon & Thomas

(57) ABSTRACT

Disclosed is an exercise amount measuring device using as an exercise signal generator an inclination detector commercially available, which can detect two-dimensional movements. Use of such inclination detectors facilitates the assembly of exercise amount measuring devices. The inclination detector 1 is connected to a counter circuit via an input circuit, and the input circuit and the counter circuit are connected to an MPU via an input-and-output port. The input circuit comprises a CR circuit or a flip-flop circuit. The counter circuit counts input pulses post-chattering exclusion, which input pulses are caused by the on-and-off switching actions, which are brought every time the contact ball touches selected contact electrodes in the inclination detector.

2 Claims, 5 Drawing Sheets

EXERCISE SIGNAL GENERATOR OF EXERCISE LOAD METER

TECHNICAL FIELD

The present invention relates to an exercise signal generator for use in an exercise amount measuring device, in which an inclination detector of the type used in cameras is used in detecting movements of a living body, thereby producing exercise signals.

BACKGROUND ART

The exercise amount measuring device is worn on a living body to detect any movements of the living body for generating exercise signals.

FIG. 6 shows a block diagram of the exercise signal generator used in a conventional exercise amount measuring device.

The exercise signal generator comprises a cantilever-like spring whip "b" having a magnet M attached to its intermediate portion and a weight "a" attached to its free end, and a sensor S such as a Hall Effect sensor, magnetic resistance element or lead switch arranged in the horizontal or vertical direction in which the magnet M moves, the sensor S being connected to an associated counter circuit C.

When one wears the exercise signal generator, the spring whip "b" bends horizontally or vertically, allowing the magnet M to come close to and leave apart from the magnetic sensor S.

The number of movements in a two-dimensional space can be determined in terms of how many times the magnet M has come to close to the magnetic sensor S while moving horizontally or vertically.

If the weight "a" is too light, any movements cannot be detected. If the spring whip "b" is too short, any movements cannot be detected, either. The weight, therefore, needs to be heavy enough to detect any movements of the living body, and likewise, the spring whip "b" needs to be long enough.

Disadvantageously this requirement enlarges the space allotted for mounting the exercise signal generator.

Also, it is required that the magnet M is so positioned that it may traverse the center of the magnetic sensor S.

To assure that the magnetic sensor S works well the parts need to be assembled with good precision.

Because of the necessity of using such extra parts the cost for manufacturing exercise signal generators is relatively high.

Incidentally inclination detectors for use in cameras are mass-produced at reduced cost, and are commercially available.

The inclination detector is responsive to the normal position, left-down, upright position, right-down, upright position, upward leaning position and downward leaning position of the camera for effecting the exposure control in respect of which direction the camera is inclined and for effecting an appropriate control on the lens drive mechanism, which is sensitive to the downward or upward leaning posture of the camera.

The inclination detector has a spherical contact body or contact ball rolling freely in its casing, and contact electrodes arranged in vertical and horizontal directions in the casing.

When the casing is inclined, the contact ball rolls in the direction in which the casing is inclined to touch a selected contact electrode, which is arranged in the inclining direction. An electric current is made to flow through the so closed switch. Thus, the direction in which the casing is inclined can be determined.

The inclination detector is responsive not only to inclinations but also to shaking movements for making its switches selectively turn on or off.

Therefore, such a simple ball-and-contact structure can be used to detect two-dimensional movements.

The inclination detector is light and small, not requiring a large space for mounting the same.

One object of the present invention is to provide an exercise amount measuring device for detecting two-dimensional movements, using an inclination detector commercially available as an exercise signal generator, thus making it easy to assemble parts into exercise amount measuring devices, which are compact and less expensive.

SUMMARY OF THE INVENTION

To attain this object an exercise signal generator means for counting movements in an exercise, comprising a casing, a spherical body rolling freely in the casing and contact switches responsive to the touching of the spherical body thereon for turning on, whereby the number of movements m the exercise may be determined judging from signals appearing at the ceasing of the exercise and from exercise signals appearing every time the rolling spherical body makes selected contact switches turn on or off.

DETAILED DESCRIPTION OF THE PREFERRED EMBODIMENT

Figure 1:
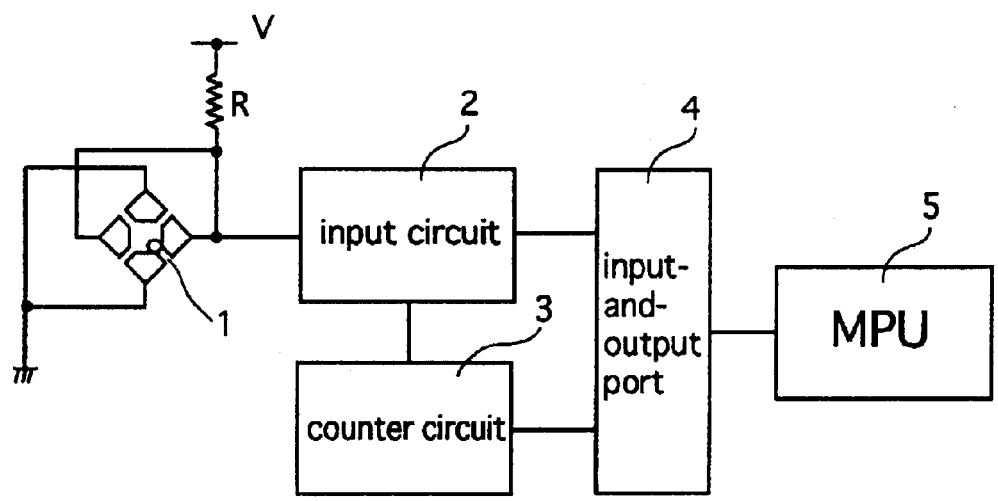
FIG. 1 is a block diagram of an exercise amount measuring device according to the present invention.

Referring to the drawings an exercise amount measuring device according to the present invention is described below.

FIG. 1 is a block diagram of the exercise amount measuring device. It comprises an inclination detector 1, an input circuit 2 connected to the inclination detector 1, a counter circuit 3 connected to the input circuit 2, an input-and-output port 4 connected to the input circuit 2 and to the counter circuit 3, and an MPU 5 connected to the input-and-output port 4.

Figure 2:
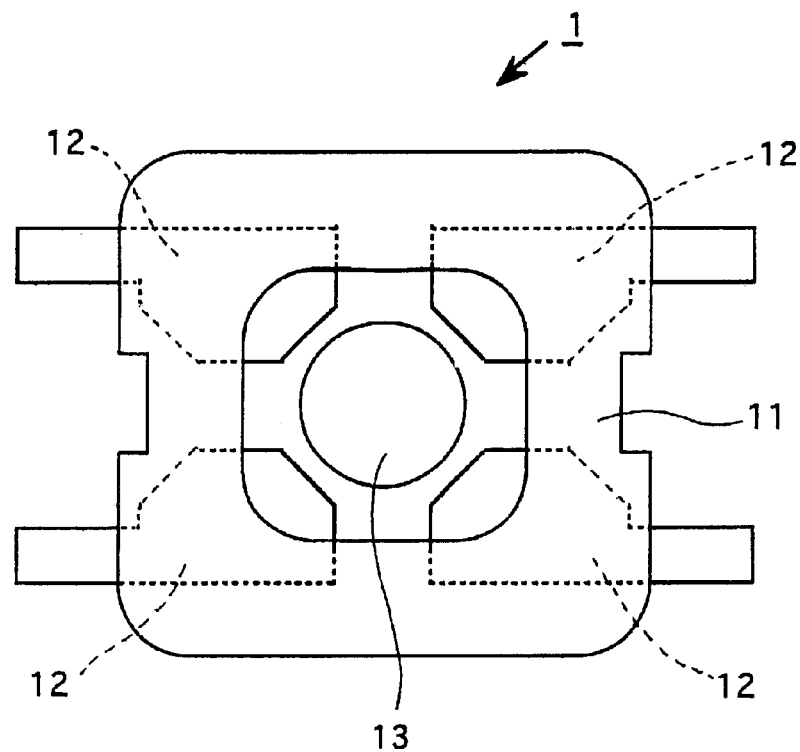
FIG. 2 is a plane view of an inclination detector used in the exercise amount measuring device.
Figure 3:
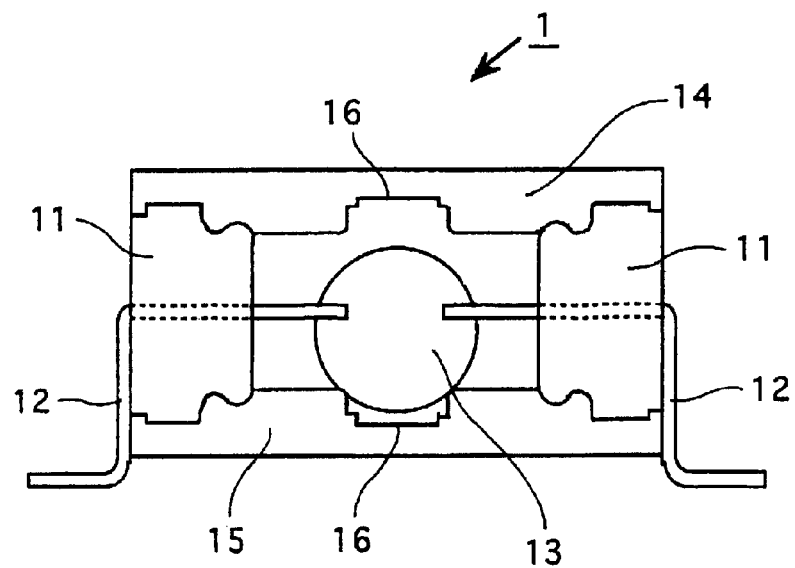
FIG. 3 is a side view of the inclination detector of FIG. 2.

Referring to FIGS. 2 and 3, the inclination detector 1 comprises an insulating casing 11 and a spherical body or contact ball 13 contained in the casing 11. The casing 11 has contact electrodes 12 embedded in its four corners. One end of each contact electrode is exposed inside, and the other end of the contact electrode is exposed outside.

The contact ball 13 can roll freely in the casing 11. The casing 11 has recesses 16 made on its ceiling and floor, thereby allowing the contact ball 13 to roll freely within the space delimited by the confronting recesses 16.

The exposed ends of the contact electrodes 12 and the contact ball 13 make up contact switches, which can turn on when the contact ball 13 touches two adjacent exposed contact pieces simultaneously, and which contact switches can turn off when the contact ball 13 leaves one or two adjacent exposed contact pieces.

The outer ends of the contact electrodes 12 projecting from the casing 11 can be used as external terminals.

The inclination detector 1 is attached to the exercise amount measuring device to be inclined at 45 degrees, and the external terminals are cross-connected to a load resistance R and to the ground.

The input circuit 2 comprises a CR circuit or flip-flop latch circuit, thereby removing the adverse effect caused by chattering when the contact ball 13 touches or leaves selected contact electrodes 12.

The counter circuit 3 counts pulses inputted postchattering exclusion, which pulses appear when selected ball-and-contact switches turn on and off.

The counter circuit 3 is responsive to a control signal from the MPU 5 for resetting.

With the arrangement as described above the exercise amount measuring device determines the exercise amount in terms of the count of pulses appearing in response to the on-and-off switching operation of the inclination detector 1.

Figure 4:
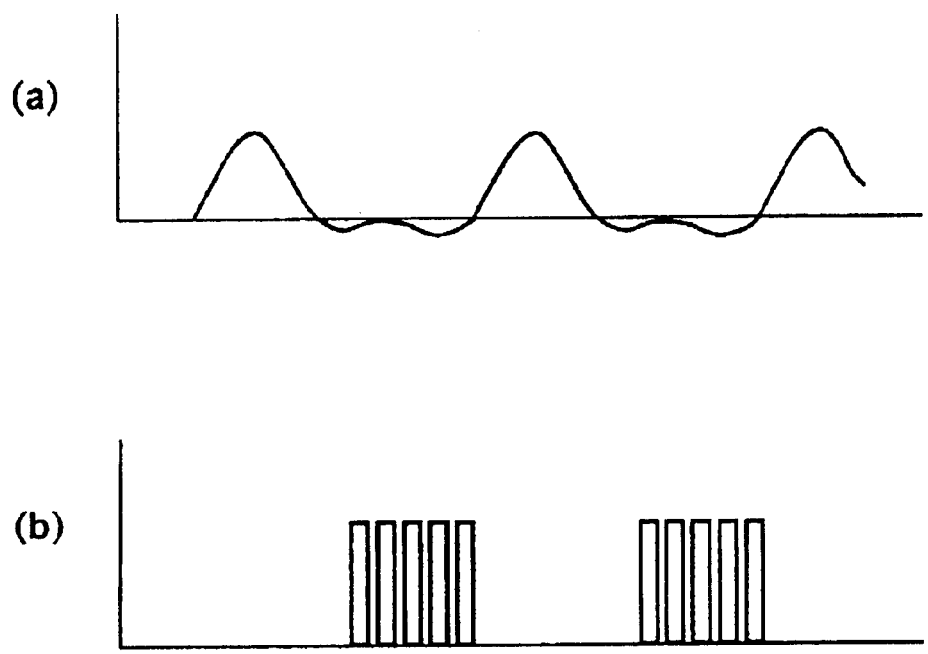
FIG. 4 shows how the acceleration of a movement changes with the movement and what input pulses appear.

FIGS. 4(*a*) and 4(*b*) show how the acceleration varies with exercise, and how pulses appear in response to the on-and-off switching operation.

As seen from FIG. 4(*a*), a large positive wave appears every time the exercise starts, and a small reaction wave appears every time the exercise ends.

While one's body remains still or when one starts to exercise, the contact ball 13 remains between two adjacent contacts 12, thus keeping the contact switch turned on, producing no pulses. When the exercise ends, the contact ball 13 rolls around to produce short pulses.

The MPU 5 judges that such short pulses appearing at the end of the exercise is counted as one, which is added to the count of movements in determining the exercise amount.

Figure 5:
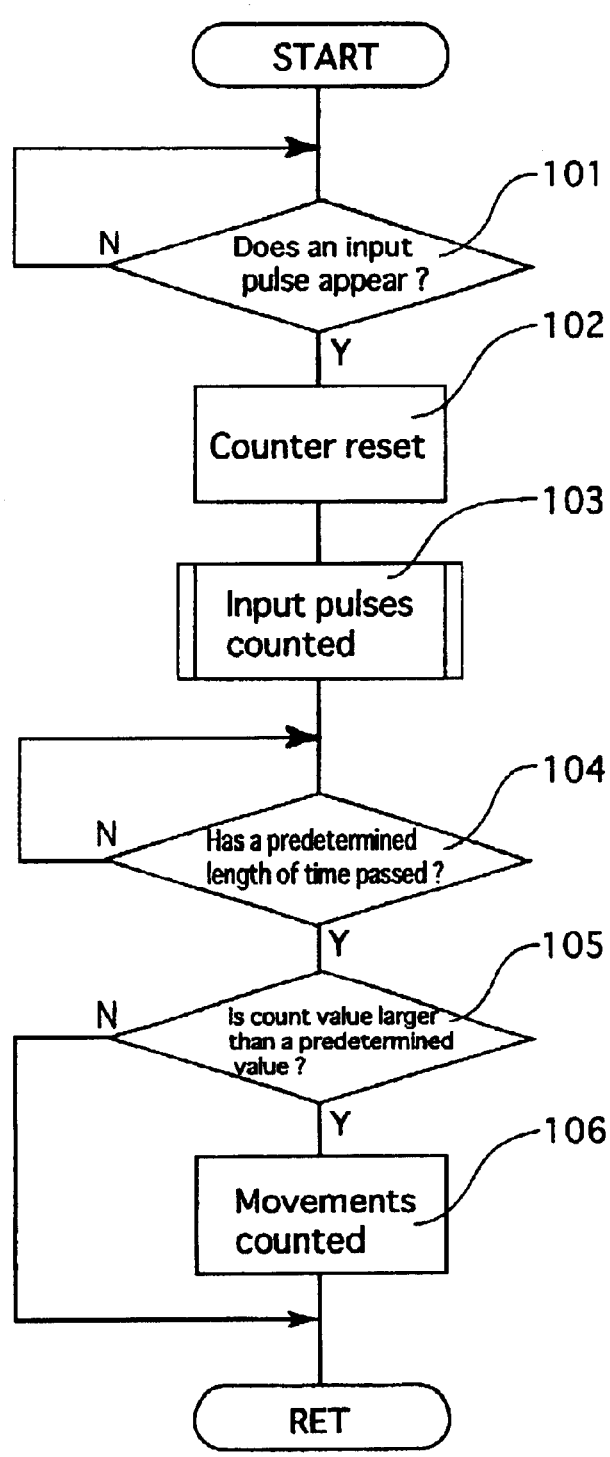
FIG. 5 is a flow chart showing the sequential steps for measuring the exercise amount.
Figure 6:
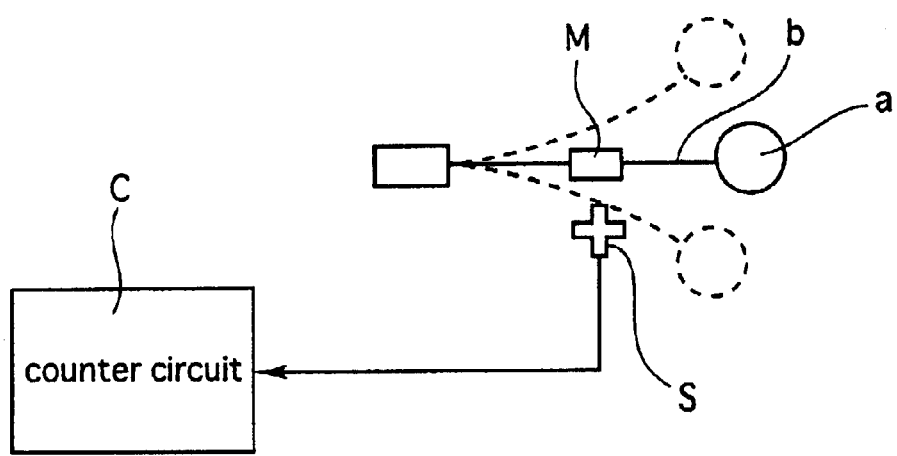
FIG. 6 is a block diagram of the exercise signal generator of a conventional exercise amount measuring device.

Referring to FIG. 5, the process conducted in the MPU 5 is described below:

When the process starts, a decision is made as to whether or not an input pulse appears (Step 101), and in the affirmative, a control signal is directed to the counter circuit 3 for resetting (Step 102), and after resetting the counter circuit 3 input pulses are counted (Step 103).

A decision is made as to whether or not a predetermined length of time has passed since the start of counting (Step 104). In the affirmative case, a decision is made as to whether or not the count value provided by the counter circuit 3 is larger than a predetermined value (Step 105).

In the affirmative case the count of the movements in the exercise plus one is outputted as the exercise amount (Step 106).

If exercise signals are replaced by signals representing steps one takes when he walks, the exercise amount measuring device can be used as a pedometer.

INDUSTRIAL APPLICABILITY

As described above, an exercise signal generator is responsive not only to the inclination of the casing but also to the shaky movement of the casing for making the spherical body roll in the casing, thereby producing exercise signals. The exercise amount can be measured no matter what type of movements may be taken in the exercise. The exercise amount measuring device can judge the exercise signals in terms of their types to count movements with accuracy, thus preventing any errors to be made in counting.

The exercise signal generator has a spherical body (contact ball) and contact switches (contact electrodes) contained in its casing, and therefore, the signal generator is single, light and small, and is easy to assemble. Accordingly, the exercise amount measuring device equipped with such an exercise signal generator is easy to assemble, and is light and compact.

What is claimed is:

1. An exercise amount measuring device, comprising:
   means for counting movements in an exercise; and
   an inclination detector, said inclination detector including: a casing; a spherical body mounted in said casing to roll freely therein; and contact switches responsive to contact with said spherical body to generate signals, whereby the number of movements may be determined judging from signals appearing when the exercise ceases and from signals appearing every time said rolling spherical body makes selected contact switches turn on or off.

2. The exercise signal generator as defined in claim 1, wherein:
   said means for counting includes: an input circuit connected to said inclination detector; a counter circuit connected to said input circuit; an input and output port connected to said input circuit and said counter circuit; and an MPU connected to said input and output port, said inclination detector adapted such that said spherical body rolls around to produce short pulses when the exercise ends and said MPU counts the short pulses as one, which is added to the count of movements in determining the exercise amount.

* * * * *